(12) United States Patent
Medoff et al.

(10) Patent No.: US 9,206,453 B2
(45) Date of Patent: Dec. 8, 2015

(54) PROCESSING BIOMASS

(71) Applicant: Xyleco, Inc., Woburn, MA (US)

(72) Inventors: Marshall Medoff, Brookline, MA (US); Harrison Medoff, Brookline, MA (US)

(73) Assignee: XYLECO, INC., Woburn, MA (US)

(*) Notice: Subject to any disclaimer, the term of this patent is extended or adjusted under 35 U.S.C. 154(b) by 0 days.

(21) Appl. No.: 13/682,936

(22) Filed: Nov. 21, 2012

(65) Prior Publication Data

US 2014/0087433 A1 Mar. 27, 2014

Related U.S. Application Data

(63) Continuation of application No. PCT/US2011/037322, filed on May 20, 2011.

(60) Provisional application No. 61/347,692, filed on May 24, 2010.

(51) Int. Cl.
*C12P 19/14* (2006.01)
*C08H 8/00* (2010.01)

(52) U.S. Cl.
CPC . *C12P 19/14* (2013.01); *C08H 8/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| 5,407,817 | A | 4/1995 | Lightsey et al. |
|---|---|---|---|
| 2002/0148575 | A1 | 10/2002 | Wingerson |
| 2009/0004715 | A1* | 1/2009 | Trimbur et al. ............... 435/166 |
| 2009/0023187 | A1 | 1/2009 | Foody |
| 2009/0061484 | A1 | 3/2009 | Scott et al. |
| 2009/0062581 | A1 | 3/2009 | Appel et al. |
| 2010/0064746 | A1 | 3/2010 | Medoff |
| 2010/0081154 | A1 | 4/2010 | Flint et al. |
| 2010/0101782 | A1 | 4/2010 | Pfeiffer et al. |

FOREIGN PATENT DOCUMENTS

| EP | 2011879 | 1/2009 |
|---|---|---|
| EP | 2098557 | 9/2009 |
| JP | S5881789 | 5/1983 |
| JP | 2000102398 | 4/2000 |
| JP | 2003514534 | 4/2003 |
| JP | 2003310288 | 11/2003 |
| JP | 2006238728 | 9/2006 |
| JP | 2010035556 | 2/2010 |
| WO | WO 2008073186 A2 * | 6/2008 |
| WO | 2008131229 | 10/2008 |
| WO | 2009046375 | 4/2009 |

OTHER PUBLICATIONS

Matsumoto et al. "Saccharification of Marine Microalgae Using Marine Bacteria for Ethanol Production", Biotechnology for Fuels and Chemicals: Applied Biochemistry and Biotechnology, edited Davison et al., Humana Press, pp. 247-254, 2003.*
John et al. "Micro and macroalgal biomass: a renewable source for bioethanol", Bioresource Technology 102: 186-193, 2011.*
Prakash et al. "Xylanse production using inexpensive agricultural wastes and its partial characterization from a halophilic *Chromohalobacter* sp. TPSV 101" World Journal of Microbiology and Biotechnology 25: 197-204, 2009.*
Search Report—Chinese Patent Application No. 2011800189639—dated May 22, 2014.

* cited by examiner

*Primary Examiner* — Taeyoon Kim
*Assistant Examiner* — Emily Cordas
(74) *Attorney, Agent, or Firm* — Leber Patent Law P.C.

(57) ABSTRACT

Biomass (e.g., plant biomass, animal biomass, and municipal waste biomass) is processed to produce useful intermediates and products, such as energy, fuels, foods or materials. For example, systems are described that can use feedstock materials, such as cellulosic and/or lignocellulosic materials, to produce an intermediate or product, e.g., by fermentation.

16 Claims, 2 Drawing Sheets

PROCESSING BIOMASS

RELATED APPLICATIONS

This application is a continuation of International Application No. PCT/US2011/037322, which designated the United States and was filed on May 20, 2011, published in English, which claims the benefit of U.S. Provisional Application Ser. No. 61/347,692, filed on May 24, 2010. The entire disclosures of the above applications are incorporated herein by reference.

BACKGROUND

Cellulosic and lignocellulosic materials are produced, processed, and used in large quantities in a number of applications. Often such materials are used once, and then discarded as waste, or are simply considered to be waste materials, e.g., sewage, bagasse, sawdust, and stover.

Various cellulosic and lignocellulosic materials, their uses, and applications have been described in U.S. Pat. Nos. 7,074,918, 6,448,307, 6,258,876, 6,207,729, 5,973,035 and 5,952,105; and in various patent applications, including "FIBROUS MATERIALS AND COMPOSITES," PCT/US2006/010648, filed on Mar. 23, 2006, AND "FIBROUS MATERIALS AND COMPOSITES," U.S. Patent Application Publication No. 2007/0045456.

SUMMARY

Generally, this invention relates to carbohydrate-containing materials (e.g., biomass materials or biomass-derived materials), methods of processing such materials to change their structure, and intermediates and products made from the structurally changed materials. Many of the methods provide materials that can be more readily utilized by a variety of microorganisms to produce useful intermediates and products, e.g., energy, a fuel such as ethanol, a food or a material.

The methods described herein utilize saltwater, and/or water containing other contaminants, impurities or pollutants, either solely or in combination with freshwater, thereby reducing or eliminating the need for a supply of fresh, uncontaminated water.

In one aspect, the invention features a method comprising utilizing a water source that is saline and/or contaminated to convert a cellulosic or lignocellulosic feedstock to an intermediate or product.

Some implementations include one or more of the following features. The feedstock may be treated to reduce its recalcitrance. For example, in some cases, the feedstock has been treated with a physical treatment selected from the group consisting of mechanical treatment, radiation, sonication, pyrolysis, oxidation, steam explosion, chemical treatment, and combinations thereof. In some cases, the feedstock has been treated with a mechanical treatment selected from the group consisting of cutting, milling, grinding, pressing, shearing and chopping.

Converting the feedstock to an intermediate or product may include contacting the feedstock with a microorganism in aqueous solution. The microorganism may be adapted to function in saline or contaminated water. For example, the microorganism may be a marine microorganism, or an engineered microorganism.

The method may further include treating the water source to reduce its salinity or contamination and utilizing the treated water in the aqueous solution. The water source may include, for example, seawater or brackish water. Additionally, or alternatively, the water source may include wastewater, grey water, collected rainwater, a microbially contaminated freshwater supply, or mixtures of any of these or of any of these with freshwater.

The biomass feedstock may, for example, be selected from the group consisting of paper, paper products, wood, wood-related materials, grasses, rice hulls, bagasse, cotton, jute, hemp, flax, bamboo, sisal, abaca, straw, corn cobs, coconut hair, algae, seaweed, microbial materials, synthetic celluloses, and mixtures thereof.

"Structurally modifying" a biomass feedstock, as that phrase is used herein, means changing the molecular structure of the feedstock in any way, including the chemical bonding arrangement, crystalline structure, or conformation of the feedstock. The change may be, for example, a change in the integrity of the crystalline structure, e.g., by microfracturing within the structure, which may not be reflected by diffractive measurements of the crystallinity of the material. Such changes in the structural integrity of the material can be measured indirectly by measuring the yield of a product at different levels of structure-modifying treatment. In addition, or alternatively, the change in the molecular structure can include changing the supramolecular structure of the material, oxidation of the material, changing an average molecular weight, changing an average crystallinity, changing a surface area, changing a degree of polymerization, changing a porosity, changing a degree of branching, grafting on other materials, changing a crystalline domain size, or changing an overall domain size.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Using the methods described herein, biomass (e.g., plant biomass, animal biomass, and municipal waste biomass) can be processed to produce useful intermediates and products such as those described herein. Systems and processes are described herein that can use as feedstock materials cellulosic and/or lignocellulosic materials that are readily available, but can be difficult to process by processes such as fermentation. Many of the processes described herein can effectively lower the recalcitrance level of the feedstock, making it easier to process, such as by bioprocessing (e.g., with any microorganism described herein, such as a homoacetogen or a heteroacetogen, and/or any enzyme described herein), thermal processing (e.g., gasification or pyrolysis) or chemical methods (e.g., acid hydrolysis or oxidation). Biomass feedstock can be treated or processed using one or more of any of the methods described herein, such as mechanical treatment, chemical treatment, radiation, sonication, oxidation, pyrolysis or steam explosion. The various treatment systems and methods can be used in combinations of two, three, or even four or more of these technologies or others described herein and elsewhere.

The methods described herein allow useful intermediates and products to be made from cellulosic and/or lignocellulosic materials, using water that contains salt and/or other contaminants. For example, the methods described herein may utilize saline water, e.g., water containing from 0.5 to 50 ppt (parts/thousand) salt (NaCl). Saline water includes seawater, which typically contains from 30-50 ppt salt, and brackish water, which typically contains from 0.5 to 30 ppt salt.

The methods described herein may also use fresh or saline water that is or may be contaminated with other materials, e.g., chemicals, heavy metals, or microbial contamination. For example, the methods may utilize wastewater, grey water, or ground or surface water that is contaminated or polluted, collected rainwater, or any combination of these sources with each other or with fresh, uncontaminated water or treated water. Any of these types of water can be used in treated, partially treated, or untreated form. Any of these types of water can be blended with fresh or treated water, e.g., in any desired ratio of contaminated to fresh or treated water, for example from about 1:1, 1:2 to 2:1, 1:5 to 5:1, 1:10 to 10:1, 1:20 to 20:1, 1:50 to 50:1, or 1:100 to 100:1.

Systems for Treating Biomass

Figure 1:
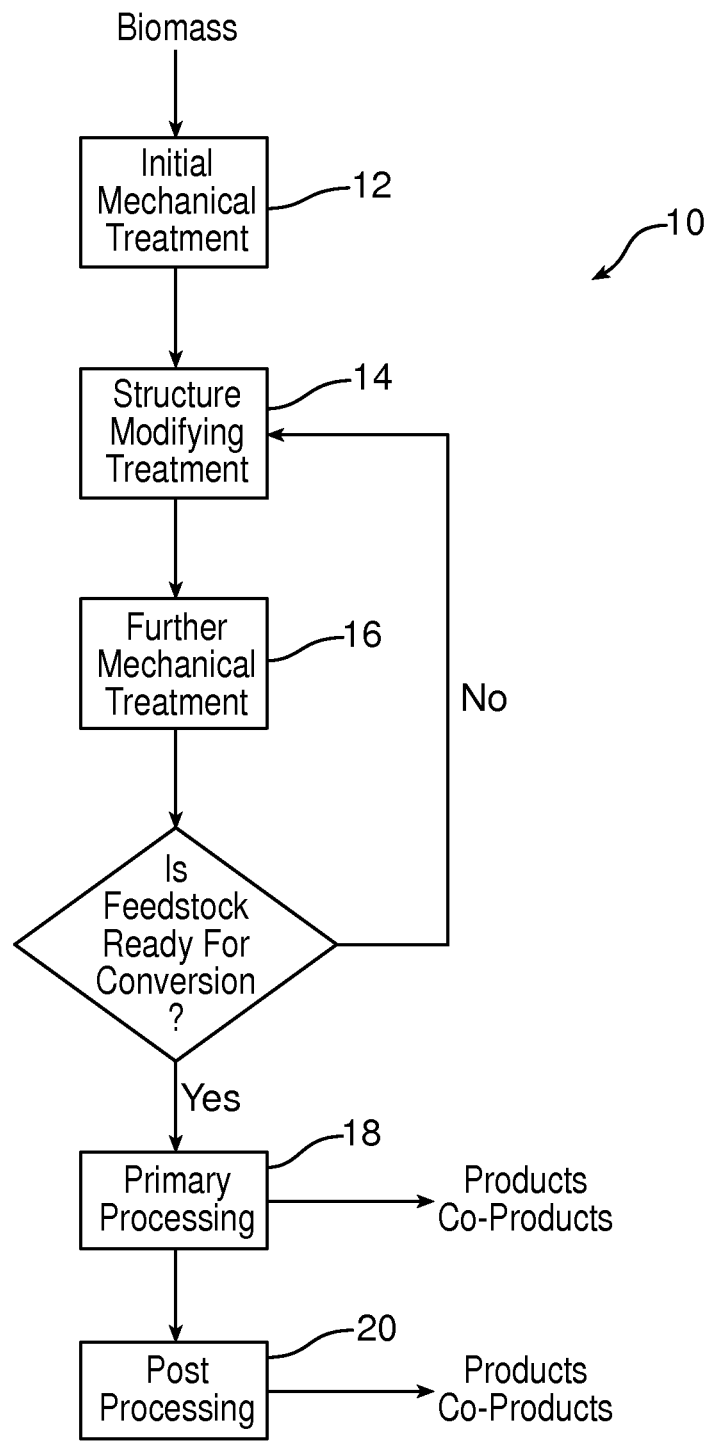
FIG. 1 is a block diagram illustrating conversion of biomass into products and co-products.

FIG. 1 shows a process 10 for converting biomass, particularly biomass with significant cellulosic and lignocellulosic components, into useful intermediates and products. Process 10 includes initially mechanically treating the feedstock (12), e.g., to reduce the size of the feedstock. The mechanically treated feedstock is then treated with a physical treatment (14) to modify its structure, for example by weakening or microfracturing bonds in the crystalline structure of the material. Next, the structurally modified material may in some cases be subjected to further mechanical treatment (16). This mechanical treatment can be the same as or different from the initial mechanical treatment. For example, the initial treatment can be a size reduction (e.g., cutting) step followed by a shearing step, while the further treatment can be a grinding or milling step.

The material can then be subjected to further structure-modifying treatment and mechanical treatment, if further structural change (e.g., reduction in recalcitrance) is desired prior to further processing.

Next, the treated material can be processed with a primary processing step 18, e.g., saccharification and/or fermentation, to produce intermediates and products (e.g., energy, fuel, foods and materials). In some cases, the output of the primary processing step is directly useful but, in other cases, requires further processing provided by a post-processing step (20). For example, in the case of an alcohol, post-processing may involve distillation and, in some cases, denaturation.

It is noted that water is used in several ways in the processes described herein. First, water is used as a medium, e.g., during saccharification and fermentation. In many cases, much of the water used in this manner can be recycled, e.g., by collecting the water removed during distillation or other post-processing. Second, water is used by the manufacturing equipment, e.g., in cooling tower and boiler systems. Water to be used in the manufacturing equipment can be contaminated and/or saline, provided that the equipment used is designed to withstand the type of water used, e.g., to be corrosion-resistant if saline water is to be used.

In some cases, the water that is used in the methods described herein, as process media and/or as cooling or boiler water, is treated to remove some or all of the contamination in the water.

For example, in the case of saline water, the water can be partially or completely desalinated, to reduce or remove the salt content, and/or can be treated to remove other contaminants such as oil, other pollutants, and/or microbial contamination.

Desalination can be performed using any desired methods. For example, desalination can be performed using membrane-based technologies, e.g., electrodialysis or reverse osmosis, or thermal technologies such as distillation, e.g., multi-stage flash distillation, multi-effect distillation, or vapor compression distillation.

When desalination is performed, brine and/or salt can be recovered as co-products of the process.

Any of the water sources described herein can be sterilized, for example using radiation (e.g., UV, electron beam), heat, oxidants (bleach, ozone), flash pasteurization, or other sterilization techniques.

If desired, the water, or intermediates or products produced using the water, can be treated with antibiotics.

Any of the water sources described herein can also be treated, before or during the processes described herein, using bioremediation.

In some cases, contaminants can be recovered as co-products. For example, metals, oil, or other chemicals or compounds can be separated from the water and recovered.

Any of these water treatment methods, or other water treatment methods, can be used to partially or completely remove or inactivate the contaminants in the water. For example, the level of contamination can be reduced to less than 10,000 ppm, less than 5,000 ppm, less than 1,000 ppm, less than 500 ppm, or less than 100 ppm.

In some cases, the water is used in an untreated form, as received from the source, e.g., using microorganisms that are adapted to function in the untreated water.

Figure 2:
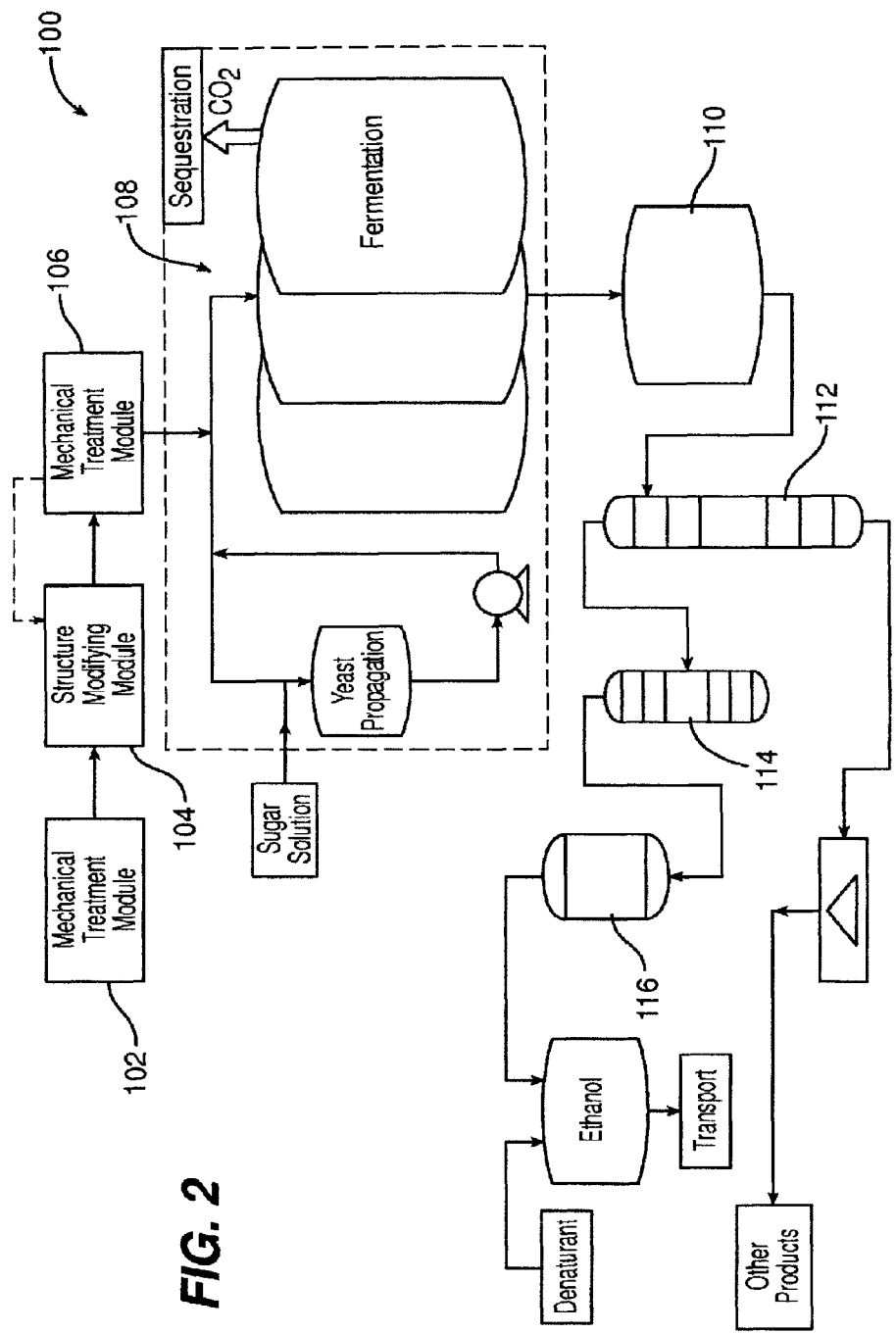
FIG. 2 is a block diagram illustrating treatment of biomass and the use of the treated biomass in a fermentation process.

FIG. 2 shows a system 100 that utilizes the steps described above for treating biomass and then using the treated biomass in a fermentation process to produce an alcohol. System 100 includes a module 102 in which a biomass feedstock is initially mechanically treated (step 12, above), a module 104 in which the mechanically treated feedstock is structurally modified (step 14, above), e.g., by irradiation, and a module 106 in which the structurally modified feedstock is subjected to further mechanical treatment (step 16, above). As discussed above, the module 106 may be of the same type as the module 102, or a different type. In some implementations the structurally modified feedstock can be returned to module 102 for further mechanical treatment rather than being further mechanically treated in a separate module 106.

After these treatments, which may be repeated as many times as required to obtain desired feedstock properties, the treated feedstock is delivered to a fermentation system 108. Mixing may be performed during fermentation, in which case the mixing is preferably relatively gentle (low shear) so as to minimize damage to shear sensitive ingredients such as enzymes and other microorganisms. In some embodiments, jet mixing is used, as described in U.S. Pat. App. Pub. 2010/0297705 by Medoff and Masterman, the complete disclosures of which are incorporated herein by reference.

Referring again to FIG. 2, fermentation produces a crude ethanol mixture, which flows into a holding tank 110. Water or other solvent, and other non-ethanol components, are stripped from the crude ethanol mixture using a stripping column 112, and the ethanol is then distilled using a distillation unit 114, e.g., a rectifier. Distillation may be by vacuum distillation. Finally, the ethanol can be dried using a molecular sieve 116 and/or denatured, if necessary, and output to a desired shipping method.

In some cases, the systems described herein, or components thereof may be portable, so that the system can be transported (e.g., by rail, truck, or marine vessel) from one location to another. The method steps described herein can be performed at one or more locations, and in some cases one or more of the steps can be performed in transit. Such mobile processing is described in U.S. Pat. App. Pub. 2010/0064746 by Medoff and International Application Publication No. WO 2008/011598 by Medoff, which designated the United States and was published in English, the full disclosures of which are incorporated herein by reference.

Any or all of the method steps described herein can be performed at ambient temperature. If desired, cooling and/or heating may be employed during certain steps. For example, the feedstock may be cooled during mechanical treatment to increase its brittleness. In some embodiments, cooling is employed before, during or after the initial mechanical treatment and/or the subsequent mechanical treatment. Cooling may be performed as described in U.S. Pat. No. 7,900,857 to Medoff, the full disclosure of which is incorporated herein by reference. Moreover, the temperature in the fermentation system 108 may be controlled to enhance saccharification and/or fermentation.

The individual steps of the methods described above, as well as the materials used, will now be described in further detail.

Physical Treatment

Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical Treatments

In some cases, methods can include mechanically treating the biomass feedstock. Mechanical treatments include, for example, cutting, milling, pressing, grinding, shearing and chopping. Milling may include, for example, ball milling, hammer milling, rotor/stator dry or wet milling, or other types of milling. Other mechanical treatments include, e.g., stone grinding, cracking, mechanical ripping or tearing, pin grinding or air attrition milling.

Mechanical treatment can be advantageous for "opening up," "stressing," breaking and shattering the cellulosic or lignocellulosic materials, making the cellulose of the materials more susceptible to chain scission and/or reduction of crystallinity. The open materials can also be more susceptible to oxidation when irradiated.

In some cases, the mechanical treatment may include an initial preparation of the feedstock as received, e.g., size reduction of materials, such as by cutting, grinding, shearing, pulverizing or chopping. For example, in some cases, loose feedstock (e.g., recycled paper, starchy materials, or switchgrass) is prepared by shearing or shredding.

Alternatively, or in addition, the feedstock material can be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the molecular structure of the material by mechanical treatment.

In some embodiments, the feedstock material is in the form of a fibrous material, and mechanical treatment includes shearing to expose fibers of the fibrous material. Shearing can be performed, for example, using a rotary knife cutter. Other methods of mechanically treating the feedstock include, for example, milling or grinding. Milling may be performed using, for example, a hammer mill, ball mill, colloid mill, conical or cone mill, disk mill, edge mill, Wiley mill or grist mill. Grinding may be performed using, for example, a stone grinder, pin grinder, coffee grinder, or burr grinder. Grinding may be provided, for example, by a reciprocating pin or other element, as is the case in a pin mill. Other mechanical treatment methods include mechanical ripping or tearing, other methods that apply pressure to the material, and air attrition milling. Suitable mechanical treatments further include any other technique that changes the molecular structure of the feedstock.

If desired, the mechanically treated material can be passed through a screen, e.g., having an average opening size of 1.59 mm or less (1/16 inch, 0.0625 inch). In some embodiments, shearing, or other mechanical treatment, and screening are performed concurrently. For example, a rotary knife cutter can be used to concurrently shear and screen the feedstock. The feedstock is sheared between stationary blades and rotating blades to provide a sheared material that passes through a screen, and is captured in a bin.

The cellulosic or lignocellulosic material can be mechanically treated in a dry state (e.g., having little or no free water on its surface), a hydrated state (e.g., having up to ten percent by weight absorbed water), or in a wet state, e.g., having between about 10 percent and about 75 percent by weight water. The fiber source can even be mechanically treated while partially or fully submerged under a liquid, such as water, ethanol or isopropanol.

The cellulosic or lignocellulosic material can also be mechanically treated under a gas (such as a stream or atmosphere of gas other than air), e.g., oxygen or nitrogen, or steam.

If desired, lignin can be removed from any of the fibrous materials that include lignin. Also, to aid in the breakdown of the materials that include cellulose, the material can be treated prior to or during mechanical treatment or irradiation with heat, a chemical (e.g., mineral acid, base or a strong oxidizer such as sodium hypochlorite) and/or an enzyme. For example, grinding can be performed in the presence of an acid.

Mechanical treatment systems can be configured to produce streams with specific morphology characteristics such as, for example, surface area, porosity, bulk density, and, in the case of fibrous feedstocks, fiber characteristics such as length-to-width ratio.

In some embodiments, a BET surface area of the mechanically treated material is greater than 0.1 $m^2/g$, e.g., greater than 0.25 $m^2/g$, greater than 0.5 $m^2/g$, greater than 1.0 $m^2/g$, greater than 1.5 $m^2/g$, greater than 1.75 $m^2/g$, greater than 5.0 $m^2/g$, greater than 10 $m^2/g$, greater than 25 $m^2/g$, greater than 35 $m^2/g$, greater than 50 $m^2/g$, greater than 60 $m^2/g$, greater than 75 $m^2/g$, greater than 100 $m^2/g$, greater than 150 $m^2/g$, greater than 200 $m^2/g$, or even greater than 250 $m^2/g$.

A porosity of the mechanically treated material can be, e.g., greater than 20 percent, greater than 25 percent, greater than 35 percent, greater than 50 percent, greater than 60 percent, greater than 70 percent, greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, after mechanical treatment the material has a bulk density of less than 0.25 g/cm$^3$, e.g., 0.20 g/cm$^3$, 0.15 g/cm$^3$, 0.10 g/cm$^3$, 0.05 g/cm$^3$ or less, e.g., 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

If the feedstock is a fibrous material the fibers of the mechanically treated material can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (e.g., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

If the feedstock is a fibrous material the average length-to-diameter ratio of fibers of the mechanically treated material can be, e.g., greater than 8/1, e.g., greater than 10/1, greater than 15/1, greater than 20/1, greater than 25/1, or greater than 50/1. An average fiber length of the mechanically treated material can be, e.g., between about 0.5 mm and 2.5 mm, e.g., between about 0.75 mm and 1.0 mm, and an average width (e.g., diameter) of the second fibrous material 14 can be, e.g., between about 5 µm and 50 µm, e.g., between about 10 µm and 30 µm.

In some embodiments, if the feedstock is a fibrous material the standard deviation of the fiber length of the mechanically treated material can be less than 60 percent of an average fiber length of the mechanically treated material, e.g., less than 50 percent of the average length, less than 40 percent of the average length, less than 25 percent of the average length, less than 10 percent of the average length, less than 5 percent of the average length, or even less than 1 percent of the average length.

In some situations, it can be desirable to prepare a low bulk density material, densify the material (e.g., to make it easier and less costly to transport to another site), and then revert the material to a lower bulk density state. Densified materials can be processed by any of the methods described herein, or any material processed by any of the methods described herein can be subsequently densified, e.g., as disclosed in WO 2008/073186 by Medoff, which designated the United States and was published in English, which is incorporated herein by reference in its entirety.

Radiation Treatment

One or more radiation processing sequences can be used to process the feedstock, and to provide a structurally modified material which functions as input to further processing steps and/or sequences. Irradiation can, for example, reduce the molecular weight and/or crystallinity of feedstock. Radiation can also sterilize the materials, or any media needed to bioprocess the material.

In some embodiments, energy deposited in a material that releases an electron from its atomic orbital is used to irradiate the materials. The radiation may be provided by (1) heavy charged particles, such as alpha particles or protons, (2) electrons, produced, for example, in beta decay or electron beam accelerators, or (3) electromagnetic radiation, for example, gamma rays, x rays, or ultraviolet rays. In one approach, radiation produced by radioactive substances can be used to irradiate the feedstock. In another approach, electromagnetic radiation (e.g., produced using electron beam emitters) can be used to irradiate the feedstock. In some embodiments, any combination in any order or concurrently of (1) through (3) may be utilized. The doses applied depend on the desired effect and the particular feedstock.

In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when maximum oxidation is desired, oxygen ions can be utilized, and when maximum nitration is desired, nitrogen ions can be utilized. The use of heavy particles and positively charged particles is described in U.S. Pat. No. 7,931,784 to Medoff, the full disclosure of which is incorporated herein by reference.

In one method, a first material that is or includes cellulose having a first number average molecular weight ($M_{N1}$ is irradiated, e.g., by treatment with ionizing radiation (e.g., in the form of gamma radiation, X-ray radiation, 100 nm to 280 nm ultraviolet (UV) light, a beam of electrons or other charged particles) to provide a second material that includes cellulose having a second number average molecular weight ($M_{N2}$) lower than the first number average molecular weight. The second material (or the first and second material) can be combined with a microorganism (with or without enzyme treatment) that can utilize the second and/or first material or its constituent sugars or lignin to produce an intermediate or product, such as those described herein.

Since the second material includes cellulose having a reduced molecular weight relative to the first material, and in some instances, a reduced crystallinity as well, the second material is generally more dispersible, swellable and/or soluble, e.g., in a solution containing a microorganism and/or an enzyme. These properties make the second material easier to process and more susceptible to chemical, enzymatic and/or biological attack relative to the first material, which can greatly improve the production rate and/or production level of a desired product, e.g., ethanol.

In some embodiments, the second number average molecular weight ($M_{N2}$) is lower than the first number average molecular weight ($M_{N1}$ by more than about 10 percent, e.g., 15, 20, 25, 30, 35, 40, 50 percent, 60 percent, or even more than about 75 percent.

In some instances, the second material includes cellulose that has a crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the carbon-containing material via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part due to their acidic nature. When particles are utilized, the particles can have the mass of a resting electron, or greater, e.g., 500, 1000, 1500, 2000, 10,000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the RHODOTRON® accelerator system, while DC type accelerators are available from RDI, now IBA Industrial, such as the DYNAMITRON® accelerator system. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy" Columbus-Ohio, ICRU-IAEA Meeting, 18-20 Mar. 2006, Iwata, Y. et al., "Alternating-Phase-Focused IH-DTL for Heavy-Ion Medical Accelerators" Proceedings of EPAC 2006, Edinburgh, Scotland and Leaner, C. M. et al., "Status of the Superconducting ECR Ion Source Venus" Proceedings of EPAC 2000, Vienna, Austria .

Gamma radiation has the advantage of a significant penetration depth into a variety of materials. Sources of gamma rays include radioactive nuclei, such as isotopes of cobalt, calcium, technetium, chromium, gallium, indium, iodine, iron, krypton, samarium, selenium, sodium, thallium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin sections of material, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. The level of depolymerization of the feedstock depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Ion Particle Beams

Particles heavier than electrons can be utilized to irradiate materials, such as carbohydrates or materials that include carbohydrates, e.g., cellulosic materials, lignocellulosic materials, starchy materials, or mixtures of any of these and others described herein. For example, protons, helium nuclei, argon ions, silicon ions, neon ions carbon ions, phosphorus ions, oxygen ions or nitrogen ions can be utilized. In some embodiments, particles heavier than electrons can induce higher amounts of chain scission (relative to lighter particles). In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

In certain embodiments, ion beams used to irradiate carbon-containing materials, e.g., biomass materials, can include more than one type of ion. For example, ion beams can include mixtures of two or more (e.g., three, four or more) different types of ions. Exemplary mixtures can include carbon ions and protons, carbon ions and oxygen ions, nitrogen ions and protons, and iron ions and protons. More generally, mixtures of any of the ions discussed above (or any other ions) can be used to form irradiating ion beams. In particular, mixtures of relatively light and relatively heavier ions can be used in a single ion beam.

In some embodiments, ion beams for irradiating materials include positively-charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to materials, initiating and sustaining cationic ring-opening chain scission reactions in an oxidative environment.

In certain embodiments, ion beams for irradiating materials include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to materials, causing anionic ring-opening chain scission reactions in a reducing environment.

In some embodiments, beams for irradiating materials can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation of biomass materials. In general, mixtures of any two or more of the above types of atoms (e.g., three or more, four or more, or even more) can be present in the beams.

In certain embodiments, ion beams used to irradiate materials include singly-charged ions such as one or more of $H^+$, $H^-$, $He^+$, $Ne^+$, $Ar^+$, $C^+$, $C^-$, $O^+$, $O^-$, $N^+$, $N^-$, $Si^+$, $Si^-$, $P^+$, $P^-$, $Na^+$, $Ca^+$, and $Fe^+$. In some embodiments, ion beams can include multiply-charged ions such as one or more of $C^{2+}$, $C^{3+}$, $C^{4+}$, $N^{3+}$, $N^{5+}$, $N^{3-}$, $O^{2+}$, $O^{2-}$, $O_2^{2-}$, $Si^{2+}$, $Si^{4+}$, $Si^{2-}$, and $Si^{4-}$. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ions. In some embodiments, the positive or negative charges can be somewhat localized over portions of the structure of the ions.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ hz, greater than $10^{17}$ hz, $10^{18}$, $10^{19}$, $10^{20}$, or even greater than $10^{21}$ hz. In some embodiments, the electromagnetic radiation has a frequency of between $10^{18}$ and $10^{22}$ hz, e.g., between $10^{19}$ to $10^{21}$ hz.

Doses

In some instances, the irradiation is performed at a dosage rate of greater than about 0.25 Mrad per second, e.g., greater than about 0.5, 0.75, 1.0, 1.5, 2.0, or even greater than about 2.5 Mrad per second. In some embodiments, the irradiating is performed at a dose rate of between 5.0 and 1500.0 kilorads/hour, e.g., between 10.0 and 750.0 kilorads/hour or between 50.0 and 350.0 kilorads/hour.

In some embodiments, the irradiating (with any radiation source or a combination of sources) is performed until the material receives a dose of at least 0.1 Mrad, at least 0.25 Mrad, e.g., at least 1.0 Mrad, at least 2.5 Mrad, at least 5.0 Mrad, at least 10.0 Mrad, at least 60 Mrad or at least 100 Mrad. In some embodiments, the irradiating is performed until the material receives a dose of from about 0.1 Mrad to about 500 Mrad, from about 0.5 Mrad to about 200 Mrad, from about 1 Mrad to about 100 Mrad, or from about 5 Mrad to about 60 Mrad. In some embodiments, a relatively low dose of radiation is applied, e.g., less than 60 Mrad.

Sonication

Sonication can reduce the molecular weight and/or crystallinity of materials, such as one or more of any of the materials described herein, e.g., one or more carbohydrate sources, such as cellulosic or lignocellulosic materials, or starchy materials. Sonication can also be used to sterilize the materials. As discussed above with regard to radiation, the process parameters used for sonication can be varied depending on various factors, e.g., depending on the lignin content of the feedstock. For example, feedstocks with higher lignin levels generally require a higher residence time and/or energy level, resulting in a higher total energy delivered to the feedstock.

In one method, a first material that includes cellulose having a first number average molecular weight ($M_{N1}$) is dispersed in a medium, such as water (e.g., saline water, waste water, or any of the other types of contaminated water described herein, with or without the addition of freshwater), and sonicated and/or otherwise cavitated, to provide a second material that includes cellulose having a second number average molecular weight ($M_{N2}$) lower than the first number average molecular weight. The second material (or the first and second material in certain embodiments) can be combined with a microorganism (with or without enzyme treatment) that can utilize the second and/or first material to produce an intermediate or product.

Since the second material includes cellulose having a reduced molecular weight relative to the first material, and in some instances, a reduced crystallinity as well, the second material is generally more dispersible, swellable, and/or soluble, e.g., in a solution containing a microorganism.

In some embodiments, the second number average molecular weight ($M_{N2}$) is lower than the first number average molecular weight ($M_{N1}$) by more than about 10 percent, e.g., 15, 20, 25, 30, 35, 40, 50 percent, 60 percent, or even more than about 75 percent.

In some instances, the second material includes cellulose that has a crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity index (prior to sonication) is from about 40 to about 87.5 percent, e.g., from about 50 to about 75 percent or from about 60 to about 70 percent, and the crystallinity index after sonication is from about 10 to about 50 percent, e.g., from about 15 to about 45 percent or from about 20 to about 40 percent. However, in certain embodiments, e.g., after extensive sonication, it is possible to have a crystallinity index of lower than 5 percent. In some embodiments, the material after sonication is substantially amorphous.

In some embodiments, the starting number average molecular weight (prior to sonication) is from about 200,000 to about 3,200,000, e.g., from about 250,000 to about 1,000,000 or from about 250,000 to about 700,000, and the number average molecular weight after sonication is from about 50,000 to about 200,000, e.g., from about 60,000 to about 150,000 or from about 70,000 to about 125,000. However, in some embodiments, e.g., after extensive sonication, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or microbial attack. In some embodiments, to increase the level of the oxidation of the second material relative to the first material, the sonication is performed in an oxidizing medium, producing a second material that is more oxidized than the first material. For example, the second material can have more hydroxyl groups, aldehyde groups, ketone groups, ester groups or carboxylic acid groups, which can increase its hydrophilicity.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and nonionic dispersing agents, e.g., poly(ethylene glycol).

In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Pyrolysis

One or more pyrolysis processing sequences can be used to process carbon-containing materials from a wide variety of different sources to extract useful substances from the materials, and to provide partially degraded materials which function as input to further processing steps and/or sequences. Pyrolysis can also be used to sterilize the materials. Pyrolysis conditions can be varied depending on the characteristics of the feedstock and/or other factors. For example, feedstocks with higher lignin levels may require a higher temperature, longer residence time, and/or introduction of higher levels of oxygen during pyrolysis.

In one example, a first material that includes cellulose having a first number average molecular weight ($M_{N1}$) is pyrolyzed, e.g., by heating the first material in a tube furnace (in the presence or absence of oxygen), to provide a second material that includes cellulose having a second number average molecular weight ($M_{N2}$) lower than the first number average molecular weight.

Since the second material includes cellulose having a reduced molecular weight relative to the first material, and in some instances, a reduced crystallinity as well, the second material is generally more dispersible, swellable and/or soluble, e.g., in a solution containing a microorganism.

In some embodiments, the second number average molecular weight ($M_{N2}$) is lower than the first number average molecular weight ($M_{N1}$) by more than about 10 percent, e.g., 15, 20, 25, 30, 35, 40, 50 percent, 60 percent, or even more than about 75 percent.

In some instances, the second material includes cellulose that has a crystallinity ($C_2$) that is lower than the crystallinity ($C_1$) of the cellulose of the first material. For example, ($C_2$) can be lower than ($C_1$) by more than about 10 percent, e.g., 15, 20, 25, 30, 35, 40, or even more than about 50 percent.

In some embodiments, the starting crystallinity (prior to pyrolysis) is from about 40 to about 87.5 percent, e.g., from about 50 to about 75 percent or from about 60 to about 70 percent, and the crystallinity index after pyrolysis is from about 10 to about 50 percent, e.g., from about 15 to about 45 percent or from about 20 to about 40 percent. However, in certain embodiments, e.g., after extensive pyrolysis, it is possible to have a crystallinity index of lower than 5 percent. In some embodiments, the material after pyrolysis is substantially amorphous.

In some embodiments, the starting number average molecular weight (prior to pyrolysis) is from about 200,000 to about 3,200,000, e.g., from about 250,000 to about 1,000,000 or from about 250,000 to about 700,000, and the number average molecular weight after pyrolysis is from about 50,000 to about 200,000, e.g., from about 60,000 to about 150,000 or from about 70,000 to about 125,000. However, in some embodiments, e.g., after extensive pyrolysis, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the susceptibility of the material to chemical, enzymatic or microbial attack. In some embodiments, to increase the level of the oxidation of the second material relative to the first material, the pyrolysis is performed in an oxidizing environment, producing a second material that is more oxidized than the first material. For example, the second material can have more hydroxyl groups, aldehyde groups, ketone groups, ester groups or carboxylic acid groups, than the first material, thereby increasing the hydrophilicity of the material.

In some embodiments, the pyrolysis of the materials is continuous. In other embodiments, the material is pyrolyzed for a pre-determined time, and then allowed to cool for a second pre-determined time before pyrolyzing again.

Oxidation

One or more oxidative processing sequences can be used to process carbon-containing materials from a wide variety of different sources to extract useful substances from the materials, and to provide partially degraded and/or altered material which functions as input to further processing steps and/or sequences. The oxidation conditions can be varied, e.g., depending on the lignin content of the feedstock, with a higher degree of oxidation generally being desired for higher lignin content feedstocks.

In one method, a first material that includes cellulose having a first number average molecular weight ($M_{N1}$) and having a first oxygen content ($O_1$) is oxidized, e.g., by heating the first material in a stream of air or oxygen-enriched air, to provide a second material that includes cellulose having a second number average molecular weight ($M_{N2}$) and having a second oxygen content ($O_2$) higher than the first oxygen content ($O_1$).

The second number average molecular weight of the second material is generally lower than the first number average molecular weight of the first material. For example, the molecular weight may be reduced to the same extent as discussed above with respect to the other physical treatments.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the first oxygen content of the first material. Oxygen content is measured by elemental analysis by pyrolyzing a sample in a furnace operating at 1300° C. or higher. A suitable elemental analyzer is the LECO™ CHNS-932 analyzer with a VTF-900 high temperature pyrolysis furnace.

Generally, oxidation of a material occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

Some oxidative methods of reducing recalcitrance in a biomass feedstock employ Fenton-type chemistry. Such methods are disclosed, for example, in U.S. Pat. App. Pub. 2010/0159569 by Medoff and Masterman, the complete disclosure of which is incorporated herein by reference.

Exemplary oxidants include peroxides, such as hydrogen peroxide and benzoyl peroxide, persulfates, such as ammonium persulfate, activated forms of oxygen, such as ozone, permanganates, such as potassium permanganate, perchlorates, such as sodium perchlorate, and hypochlorites, such as sodium hypochlorite (household bleach).

In some situations, pH is maintained at or below about 5.5 during contact, such as between 1 and 5, between 2 and 5, between 2.5 and 5 or between about 3 and 5. Oxidation conditions can also include a contact period of between 2 and 12 hours, e.g., between 4 and 10 hours or between 5 and 8 hours. In some instances, temperature is maintained at or below 300° C., e.g., at or below 250, 200, 150, 100 or 50° C. In some instances, the temperature remains substantially ambient, e.g., at or about 20-25° C.

In some embodiments, the one or more oxidants are applied as a gas, such as by generating ozone in-situ by irradiating the material through air with a beam of particles, such as electrons.

In some embodiments, the mixture further includes one or more hydroquinones, such as 2,5-dimethoxyhydroquinone (DMHQ) and/or one or more benzoquinones, such as 2,5-dimethoxy-1,4-benzoquinone (DMBQ), which can aid in electron transfer reactions.

In some embodiments, the one or more oxidants are electrochemically-generated in-situ. For example, hydrogen peroxide and/or ozone can be electro-chemically produced within a contact or reaction vessel.

Other Processes to Solubilize, Reduce Recalcitrance or to Functionalize

Any of the processes of this paragraph can be used alone without any of the processes described herein, or in combination with any of the processes described herein (in any order): steam explosion, chemical treatment (e.g., acid treatment (including concentrated and dilute acid treatment with mineral acids, such as sulfuric acid, hydrochloric acid and organic acids, such as trifluoroacetic acid) and/or base treatment (e.g., treatment with lime or sodium hydroxide)), UV treatment, screw extrusion treatment (see, e.g., International Application Publication No. WO 2010/056940 by Medoff, which designated the Unites States and was published in English, which is incorporated herein by reference in its entirety), solvent treatment (e.g., treatment with ionic liquids) and freeze milling (see, e.g., U.S. Pat. No. 7,900,857 to Medoff, which is incorporated herein by reference in its entirety).

Production of Fuels, Acids, Esters and/or Other Products

A typical biomass resource contains cellulose, hemicellulose, and lignin plus lesser amounts of proteins, extractables and minerals. After one or more of the processing steps discussed above have been performed on the biomass, the complex carbohydrates contained in the cellulose and hemicellulose fractions can in some cases be processed into fermentable sugars, optionally, along with acid or enzymatic hydrolysis. The sugars liberated can be converted into a variety of products, such as alcohols or organic acids. The product obtained depends upon the microorganism utilized and the conditions under which the bioprocessing occurs. In other embodiments, the treated biomass material can be subjected to thermochemical conversion, or other processing.

Examples of methods of further processing the treated biomass material are discussed in the following sections.

Saccharification

In order to convert the treated feedstock to a form that can be readily fermented, in some implementations the cellulose in the feedstock is first hydrolyzed to low molecular weight carbohydrates, such as sugars, by a saccharifying agent, e.g., an enzyme, a process referred to as saccharification. In some implementations, the saccharifying agent comprises an acid, e.g., a mineral acid. When an acid is used, co-products may be generated that are toxic to microorganisms, in which case the process can further include removing such co-products. Removal may be performed using an activated carbon, e.g., activated charcoal, or other suitable techniques.

The materials that include the cellulose are treated with the enzyme, e.g., by combining the material and the enzyme in a solvent, e.g., in an aqueous solution.

Enzymes and biomass-destroying organisms that break down biomass, such as the cellulose and/or the lignin portions of the biomass, contain or manufacture various cellulolytic enzymes (cellulases), ligninases or various small molecule biomass-destroying metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (β-glucosidases). A cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally cellobiase cleaves cellobiose to yield glucose.

Fermentation

Microorganisms can produce a number of useful intermediates and products by fermenting a low molecular weight sugar produced by saccharifying the treated biomass materials. For example, fermentation or other bioprocesses can produce alcohols, organic acids, hydrocarbons, hydrogen, proteins or mixtures of any of these materials.

Yeast and *Zymomonas* bacteria, for example, can be used for fermentation or conversion. Other microorganisms are discussed in the Materials section, below. The optimum pH for yeast is from about pH 4 to 5, while the optimum pH for *Zymomonas* is from about pH 5 to 6. Typical fermentation times are about 24 to 96 hours with temperatures in the range of 26° C. to 40° C., however thermophilic microorganisms prefer higher temperatures.

Mobile fermentors can be utilized, as described in International Application Publication No. WO 2008/011598 by Medoff, which designated the United States and was published in English, which is incorporated herein by reference in its entirety. Similarly, the saccharification equipment can be mobile. Further, saccharification and/or fermentation may be performed in part or entirely during transit.

Thermochemical Conversion

Thermochemical conversion can be performed on the treated biomass to produce one or more desired intermediates and/or products. A thermochemical conversion process includes changing molecular structures of carbon-containing material at elevated temperatures. Specific examples include gasification, pyrolysis, reformation, partial oxidation and mixtures of these (in any order).

Gasification converts carbon-containing materials into a synthesis gas (syngas), which can include methanol, carbon monoxide, carbon dioxide and hydrogen. Many microorganisms, such as acetogens or homoacetogens are capable of utilizing a syngas from the thermochemical conversion of biomass, to produce a product that includes an alcohol, a carboxylic acid, a salt of a carboxylic acid, a carboxylic acid ester or a mixture of any of these. Gasification of biomass (e.g., cellulosic or lignocellulosic materials), can be accomplished by a variety of techniques. For example, gasification can be accomplished utilizing staged steam reformation with a fluidized-bed reactor in which the carbonaceous material is first pyrolyzed in the absence of oxygen and then the pyrolysis vapors are reformed to synthesis gas with steam providing added hydrogen and oxygen. In such a technique, process heat comes from burning char. Another technique utilizes a screw auger reactor in which moisture and oxygen are introduced at the pyrolysis stage and the process heat is generated from burning some of the gas produced in the latter stage. Another technique utilizes entrained flow reformation in which both external steam and air are introduced in a single-stage gasification reactor. In partial oxidation gasification, pure oxygen is utilized with no steam.

Post-Processing

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Intermediates and Products

Using, e.g., such primary processes and/or post-processing, the treated biomass can be converted to one or more products, such as energy, fuels, foods and materials. Other examples include carboxylic acids, such as acetic acid or butyric acid, salts of a carboxylic acid, a mixture of carboxylic acids and salts of carboxylic acids and esters of carboxylic acids (e.g., methyl, ethyl and n-propyl esters), ketones, aldehydes, alpha, beta unsaturated acids, such as acrylic acid and olefins, such as ethylene. Other alcohols and alcohol derivatives include propanol, propylene glycol, 1,4-butanediol, 1,3-propanediol, methyl or ethyl esters of any of these alcohols. Other products include methyl acrylate, methylmethacrylate, lactic acid, propionic acid, butyric acid, succinic acid, 3-hydroxypropionic acid, a salt of any of the acids and a mixture of any of the acids and respective salts.

Other intermediates and products, including food and pharmaceutical products, are described in U.S. Pat. App. Pub. 2010/0124583 by Medoff, the full disclosure of which is hereby incorporated by reference herein.

Materials

Biomass Materials

The biomass can be, e.g., a cellulosic or lignocellulosic material. Such materials include paper and paper products (e.g., polycoated paper and Kraft paper), wood, wood-related materials, e.g., particle board, grasses, rice hulls, bagasse, jute, hemp, flax, bamboo, sisal, abaca, straw, switchgrass, alfalfa, hay, corn cobs, corn stover, coconut hair; and materials high in α-cellulose content, e.g., cotton. Feedstocks can be obtained from virgin scrap textile materials, e.g., remnants, post consumer waste, e.g., rags. When paper products are used they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Biomass feedstocks can also be obtained or derived from human (e.g., sewage), animal or plant wastes. Additional cellulosic and lignocellulosic materials have been described in U.S. Pat. Nos. 6,448,307, 6,258, 876, 6,207,729, 5,973,035 and 5,952,105.

In some embodiments, the biomass material includes a carbohydrate that is or includes a material having one or more β-1,4-linkages and having a number average molecular weight between about 3,000 and 50,000. Such a carbohydrate is or includes cellulose (I), which is derived from (β-glucose 1) through condensation of β(1,4)-glycosidic bonds. This linkage contrasts itself with that for α(1,4)-glycosidic bonds present in starch and other carbohydrates.

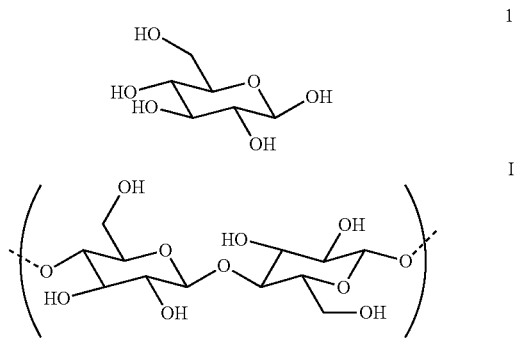

In some implementations starchy materials may be used. Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials.

Other suitable biomass materials include sugars, sugarcane, sugarcane extracts, and bagasse.

In some cases the biomass is a microbial material. Microbial sources include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such as alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Saccharifying Agents

Cellulases are capable of degrading biomass, and may be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used.

Fermentation Agents

The microorganism(s) used in fermentation can be natural microorganisms and/or engineered microorganisms. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

Suitable fermenting microorganisms have the ability to convert carbohydrates, such as glucose, xylose, arabinose, mannose, galactose, oligosaccharides or polysaccharides into fermentation products. Fermenting microorganisms include strains of the genus *Sacchromyces* spp. e.g., *Sacchromyces cerevisiae* (baker's yeast), *Saccharomyces distaticus, Saccharomyces uvarum*; the genus *Kluyveromyces*, e.g., species *Kluyveromyces marxianus, Kluyveromyces fragilis*; the genus *Candida*, e.g., *Candida pseudotropicalis*, and *Candida brassicae, Pichia stipitis* (a relative of *Candida shehatae*, the genus *Clavispora*, e.g., species *Clavispora lusitaniae* and *Clavispora opuntiae* the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212).

Commercially available yeasts include, for example, RED STAR®/LESAFFRE ETHANOL RED yeast (available from Red Star/Lesaffre, USA),. FALI® yeast (available from Fleischmann's Yeast, a division of Burns Philip Food Inc., USA), SUPERSTART® yeast (available from Alltech, now Lalemand), GERT STRAND® yeast (available from Gert Strand AB, Sweden) and FERMOL® yeast (available from DSM Specialties).

Bacteria may also be used in fermentation, e.g., *Zymomonas mobilis* and *Clostridium thermocellum* (Philippidis, 1996, supra).

Adapted Microorganisms for Saccharification and/or Fermentation

The microorganisms used in saccharification and/or fermentation can be genetically adapted to tolerate salinity and/or contamination in the water source. For example, the microorganisms can be extremophiles.

In some cases, the microorganisms are halophilic or halotolerant organisms, adapted to function under saline conditions. Such microorganisms include halobacteria, for example marine bacteria, e.g., amylase-producing bacteria such as *Pseudoalterimonas undina* NKMB 0074, and *chromohalobacter* sp., e.g., *chromohalobacter* sp. TVSP 101 and *chromohalobacter beijerinkckii*. Examples of halobacteria include *Haloarcula hispanica, Micrococcus halobius, Micrococcus varians* subspecies *halophilus, Halobacterium salinarum, Natronococcus* sp. strain Ah-36, *Halomonas meridiana*, and *Bacillus dipsosauri*. Other halotolerant and halophilic microorganisms include those that are used to ferment food products in salt solutions, for example *Aspergillus sojae, Aspergillus oryzae, Saccharomyces rouxii, Zycosaccharomyces rouxii, Candida etchellsii, Candida versatilis*, and *Torulopsis versatilis*.

In other cases, the microorganisms may be metabolically or otherwise engineered to function in the saline and/or contaminated water source.

It may be desirable to utilize a combination of microorganisms in a mixed culture, as such cultures are often better able to withstand contamination. In some cases, the mixture of microorganisms can include microorganisms adapted to digest contaminants in the water, e.g., microbial cultures used in bioremediation, and microorganisms adapted to saccharify the cellulosic and/or lignocellulosic feedstock and/or ferment sugars. The different microorganisms can be added, for example, as a mixture, separately, or sequentially.

OTHER EMBODIMENTS

A number of embodiments of the invention have been described. Nevertheless, it will be understood that various modifications may be made without departing from the spirit and scope of the invention.

For example, the process parameters of any of the processing steps discussed herein can be adjusted based on the lignin content of the feedstock, for example as disclosed in U.S. Pat.

App. Pub. 2010/0203495 by Medoff and Masterman, the full disclosure of which is incorporated herein by reference.

While it is possible to perform all the processes described herein all at one physical location, in some embodiments, the processes are completed at multiple sites, and/or may be performed during transport.

Lignin liberated in any process described herein can be captured and utilized. For example, the lignin can be used as captured as a plastic, or it can be synthetically upgraded to other plastics. In some instances, it can be utilized as an energy source, e.g., burned to provide heat. In some instances, it can also be converted to lignosulfonates, which can be utilized as binders, dispersants, emulsifiers or as sequestrants. Measurement of the lignin content of the starting feedstock can be used in process control in such lignin-capturing processes.

When used as a binder, the lignin or a lignosulfonate can, e.g., be utilized in coal briquettes, in ceramics, for binding carbon black, for binding fertilizers and herbicides, as a dust suppressant, in the making of plywood and particle board, for binding animal feeds, as a binder for fiberglass, as a binder in linoleum paste and as a soil stabilizer.

As a dispersant, the lignin or lignosulfonates can be used, e.g., concrete mixes, clay and ceramics, dyes and pigments, leather tanning and in gypsum board.

As an emulsifier, the lignin or lignosulfonates can be used, e.g., in asphalt, pigments and dyes, pesticides and wax emulsions.

As a sequestrant, the lignin or lignosulfonates can be used, e.g., in micro-nutrient systems, cleaning compounds and water treatment systems, e.g., for boiler and cooling systems.

As a heating source, lignin generally has a higher energy content than holocellulose (cellulose and hemicellulose) since it contains more carbon than homocellulose. For example, dry lignin can have an energy content of between about 11,000 and 12,500 BTU per pound, compared to 7,000 an 8,000 BTU per pound of holocellulose. As such, lignin can be densified and converted into briquettes and pellets for burning. For example, the lignin can be converted into pellets by any method described herein. For a slower burning pellet or briquette, the lignin can be crosslinked, such as applying a radiation dose of between about 0.5 Mrad and 5 Mrad. Crosslinking can make a slower burning form factor. The form factor, such as a pellet or briquette, can be converted to a "synthetic coal" or charcoal by pyrolyzing in the absence of air, e.g., at between 400 and 950° C. Prior to pyrolyzing, it can be desirable to crosslink the lignin to maintain structural integrity.

Accordingly, other embodiments are within the scope of the following claims.

What is claimed is:

1. A method comprising:
providing a lignocellulosic feedstock;
combining the feedstock with saline water having an NaCl concentration of from 0.5 to 50 ppt; and
saccharifying the feedstock in the saline water, utilizing an enzyme comprising a cellulase, to produce a sugar solution comprising glucose.

2. The method of claim 1 wherein the feedstock has been treated to reduce its recalcitrance.

3. The method of claim 1 further comprising contacting the feedstock with a microorganism in aqueous solution during or after saccharifying.

4. The method of claim 3 further comprising treating the saline water to reduce its salinity and utilizing the treated water in the aqueous solution.

5. The method of claim 1 wherein the water source comprises seawater or brackish water.

6. The method of claim 1 wherein the water source comprises wastewater, grey water, or collected rainwater.

7. The method of claim 1 wherein the water source comprises a microbially contaminated freshwater supply.

8. The method of claim 2 wherein the feedstock has been treated with a physical treatment selected from the group consisting of mechanical treatment, radiation, sonication, pyrolysis, oxidation, steam explosion, chemical treatment, and combinations thereof.

9. The method of claim 8 wherein the feedstock has been treated with a mechanical treatment selected from the group consisting of cutting, milling, grinding, pressing, shearing and chopping.

10. The method of claim 1 wherein the feedstock is corn cobs.

11. The method of claim 3 wherein the microorganism comprises a marine microorganism.

12. The method of claim 3 wherein the microorganism comprises an engineered microorganism.

13. The method of claim 3, where the microorganism is a bacterium.

14. The method of claim 3, where the microorganism is a fungus.

15. The method of claim 4, where the saline water is diluted with fresh or treated water in the ratio of 1 to 5 to 5 to 1 to reduce its salinity.

16. The method of claim 3 wherein the microorganism is a halophilic or halotolerant microorganism.

* * * * *